United States Patent [19]

Hulka et al.

[11] 4,112,951
[45] Sep. 12, 1978

[54] SURGICAL CLIP
[75] Inventors: Jaroslav Fabian Hulka, Chapel Hill, N.C.; George Selden Clemens, Northfield, Ill.
[73] Assignee: Research Corporation, New York, N.Y.
[21] Appl. No.: 652,616
[22] Filed: Jan. 26, 1976
[51] Int. Cl.² ............................................. A61B 17/12
[52] U.S. Cl. ....................................... 128/346; 24/251; 128/325
[58] Field of Search ................... 24/251; 128/321, 325, 128/346; 339/255 P, 261; 251/9
[56]  References Cited
U.S. PATENT DOCUMENTS

| 475,257 | 5/1892 | Thuge | 24/251 UX |
|---|---|---|---|
| 1,832,879 | 11/1931 | Ruskin | 128/321 |
| 2,036,461 | 4/1936 | Darby | 339/255 P X |
| 3,090,029 | 5/1963 | Stroebel | 339/255 P |
| 3,398,746 | 8/1968 | Abramson | 128/321 X |
| 3,687,131 | 8/1972 | Rayport et al. | 128/346 X |
| 3,882,854 | 5/1975 | Hulka et al. | 128/6 |
| 3,950,829 | 4/1976 | Cohen | 24/251 X |
| 4,064,881 | 12/1977 | Meredith | 128/325 |

FOREIGN PATENT DOCUMENTS

D971,659  6/1975  United Kingdom ................ 128/346

*Primary Examiner*—Robert W. Michell
*Assistant Examiner*—Michael H. Thaler
*Attorney, Agent, or Firm*—Harold L. Stowell

[57] ABSTRACT

A surgical clip, particularly adapted to produce necrosis in Fallopian tube tissue, consists of jaws hinged adjacent one end and a U-shaped spring which holds the jaws open in one position and exerts a closing pressure on the jaws in another position. When the spring is in the jaws closing position, the bridge portion thereof in conjunction with side flanges carried by one of the jaws provides a smoothly contoured hinge end thereby reducing to a minimum zones for the entrapment of tissue which might be the cause of adhesions.

5 Claims, 4 Drawing Figures

SURGICAL CLIP

The Government has rights in this invention pursuant to Contract No. AID/csd-2979 awarded by the Agency for International Development.

BACKGROUND OF THE INVENTION

1. Field of the Invention

This invention generally appertains to new and useful improvements in clamping devices, especially those designed for closing or shutting off flexible tubular conduits, and is particularly directed to a new and useful clamping instrument for use for occluding Fallopian tubes and other ducts in an animal or a human body.

2. State of the Art

In our U.S. Pat. No. 3,882,854 there is shown and described a hinged jaw type clip or clamp designed such that the upper and lower jaws of the clip are closed down on the Fallopian tube to an open height of 1 mm at the forward end of the clip, at which point a strong compressive force is applied through a U-shaped spring. This force causes gradual necrosis and dissipation of the tissue between the jaws so that the clip effects a complete closure, upon completion of the necrosis of the tube, both without hemorrhaging and without any open spaces through which live tissue and/or ova could pass.

Our said patent also discloses a clip applicator which comprises a laparoscope adapted to receive the clip at its extended end and a pair of jaw and spring actuating rams. The laparoscope may also include a surgical microscope and a source of light which may comprise a light transmitting fiber optical bundle.

SUMMARY OF THE INVENTION

The present invention is directed to an improved clip or clamp of the type disclosed in U.S. Pat. No. 3,882,854 and for use in the applicator previously invented by us and described and claimed in our said U.S. Pat. No. 3,882,854. The invention may be generally defined as a surgical clip for occluding tubes in a living animal, sid clip comprising first and second jaw members and pivotal mounting means adjacent one end of each jaw member. Said pivotal mounting means includes a pair of side flanges at said one end of the first jaw member, an arcuate recess between said side flanges and a pivot pin receiving bore in said side flanges the axis of which lies on a radius of the arcuate recess. Said one end of the second jaw member has a width to be snugly received between the pair of side flanges of said first jaw member. A depending arcuate bearing element is formed on said second jaw member and is adapted to be received in the arcuate recess in the first jaw member. A pivot pin receiving bore is formed in the arcuate bearing element and a pivot pin is positioned in said bore in said flanges and the bore in the arcuate bearing element. A generally U-shaped spring member engages the remote surfaces of each jaw member and is slidable from a first position on one side of the pivotal mounting to urge said jaw members into the open arrangement, to a second position on the other side of said pivotal mounting, to urge said jaw members into the closed position. When the spring member is in the jaws closing position, the bridge portion thereof in conjunction with said side flanges carried by said first jaw member provides a smoothly contoured hinge end for the clip thereby reducing to a minimum zones for the entrapment of tissue which might be the cause of adhesions.

DESCRIPTION OF THE DRAWING

The invention will be more particularly described in reference to the accompanying drawing wherein.

DESCRIPTION OF THE PREFERRED EMBODIMENT

Figure 1:
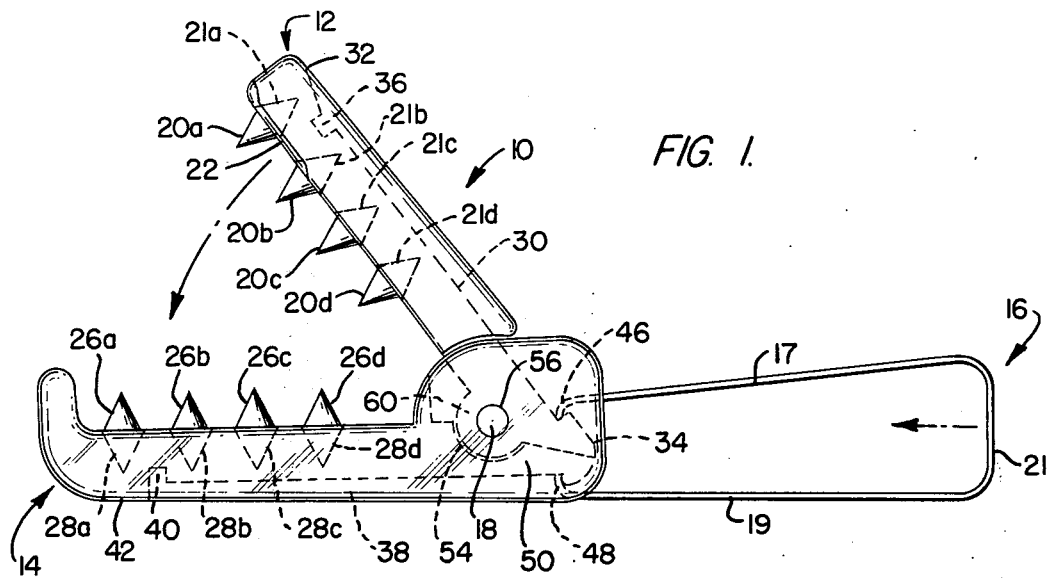
FIG. 1 is an enlarged side view of an embodiment of a tube clip of the invention with the clip jaws in the open position and being retained therein by a generally U-shaped spring.
Figure 2:
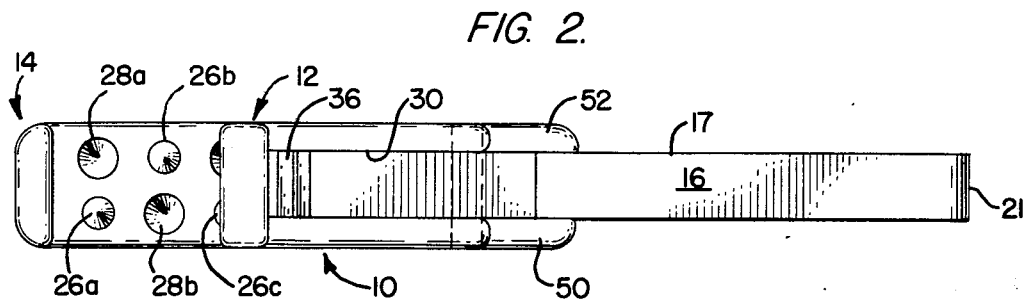
FIG. 2 is a top plan view of the structure shown in FIG. 1.

Referring to the drawings, 10 generally designates the improved Fallopian tube clip or clamp. The clip 10 includes an upper jaw member 12, a lower jaw member 14 and a U-shaped spring assembly 16. The upper and lower jaws 12 and 14 of the clip are hinged together by a hinge pin 18 which pin may be made of stainless steel, gold, plastic or other biocompatible material while the jaws 12 and 14 are also formed of a biocompatible material. Lexan plastic has been found to be very suitable, and comprises a thermoplastic polycarbonate resin manufactured by General Electric Company.

The upper jaw 12 is molded or formed with a plurality of depending conical spikes 20a, b, c and d arranged in two rows with spikes 20a and c aligned in one row and 20b and d in the other row. Further, the surface 22 of upper jaw 12 is provided with four conical bores 21a, b, c, and d with two of the bores being in the same row with conical spikes 20b and 20d and the other conical bores being in the same row as conical spikes 20a and 20c. The spikes prevent the clip from slipping off the slippery Fallopian tube as the jaws of the clip are closed by the closure tool, and prevent extrusion of the Fallopian tube from the forward end of the clip.

The lower jaw 14 is also provided with alternate spikes and bores spaced and arranged such that, when the jaws are closed, spikes in the top jaw engage bores in the lower jaw and vice versa. In the bottom jaw, the spikes are designated 26a, 26b, 26c and 26d and the conical bores are designated 28a, b, c and d.

The upper jaw 12 is provided with a groove 30 in its top surface 32 which extends from adjacent to the rear end 34 to a transverse slot 36. The groove 30 and the transverse slot 36 are sized to receive the U-shaped spring 16 to be more fully described hereinafter. A similar groove 38 and slot 40 are formed in the bottom surface 42 of the lower jaw 14 of the clip.

The U-shaped spring assembly 16 comprises a pair of legs 17 and 19 and a bridge member 21. The ends of its legs 17 and 19 are turned in as at 46 and 48. The width of the spring is such that it is slidably receivable in the grooves 30 and 38 in the respective jaws 12 and 14 and the spring has a thickness so that the turned-in ends 46 and 48 may be received in their respective slots 36 and 40 in jaws 12 and 14.

THE IMPROVED HINGE ASSEMBLY

The lower jaw 14 has a pair of said flanges 50 and 52 between which lies an arcuate recess 54. The circular arc of recess 54 is concentric with the center of pivot pin 18, which pin 18 is received in bores 56 and 56' in side flanges 50 and 52 respectively.

The hinge end 34 of jaw member 12 has a width such that it can be snugly but movably received between the pair of flanges 50 and 52 on jaw member 14. Further, the hinge end 34 is shaped to provide a depending arcuate bearing element 60. The radius of curvature of the depending arcuate bearing element 60 is fractionally less than the radius of curvature of the arcuate recess 54 in jaw member 14.

The depending arcuate bearing element 60 is bored to receive the pivot pin 18.

Figure 3:
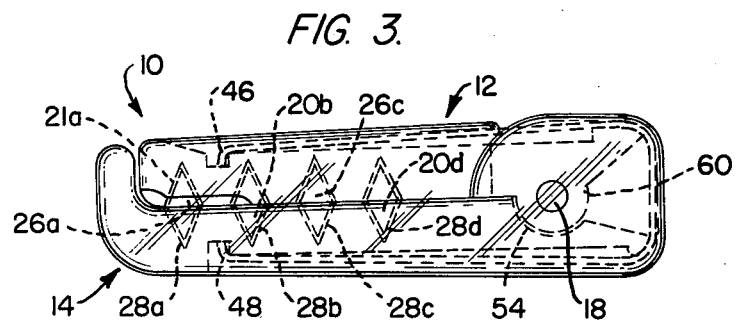
FIG. 3 is a view of the clip shown in FIG. 1 with the jaws in the closed position and being retained therein by the U-shaped spring.
Figure 4:
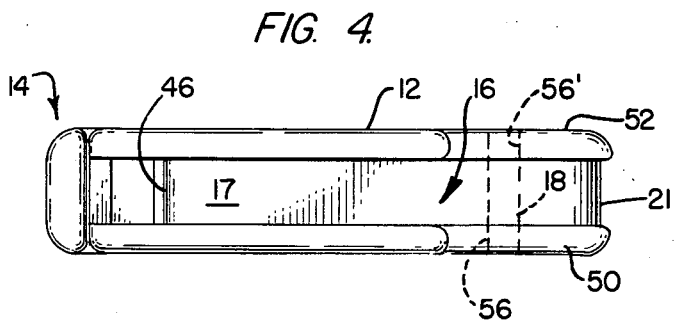
FIG. 4 is a top plan view of the structure shown in FIG. 3.

With this arrangement of parts, when the spring member 16 is in the jaws closing position, the bridge portion 21 thereof in conjunction with said side flanges 50 and 52 carried by the lower jaw member 14 provides a smoothly contoured hinge end thereby reducing to a minimum zones for the entrapment of tissue which might be the cause of adhesions as more clearly shown in FIGS. 3 and 4.

The improved clip of this invention would generally be used in conjunction with the laparoscope clip applicator shown, described and claimed in our U.S. Patent No. 3,882,854.

From the foregoing description of the improved Fallopian tube clip, it will be seen by those skilled in the art that the aims and objects of the present invention are fully accomplished.

We claim:

1. A surgical clip for occluding tubes in a living animal, said clip comprising first and second jaw members; means adjacent one end of each jaw member for pivotally mounting the other ends of said jaw members for movement toward each other to a closed position and away from each other to an open position; said pivotal mounting means including a pair of side flanges at said one end of the first jaw member, an arcuate recess between said side flanges, a pivot pin receiving bore in said side flanges the axis of which lies on a radius of said arcuate recess, said one end of the second jaw member having a width to be snugly received between the pair of side flanges of said first jaw member, an arcuate bearing element on said second jaw member adapted to be received in the arcuate recess of the first member, a transverse pivot pin receiving bore in the arcuate bearing element, the axis of said pivot pin receiving bore lying on a radius of the bearing element and co-axial with the bores in the side flanges and a pivot pin in said bore in side flanges and the bore in the arcuate bearing element; a generally U-shaped spring member consisting of a pair of legs and a connecting bridge portion, the pair of legs engaging remote surfaces of each jaw member and slidable from a first position on one side of the pivotal mounting to urge said jaw members into the open position to a second position on the other side of said pivotal mounting, to urge said jaw members into the closed position and, when the spring member is in the jaws closing position, the free end of each of the pair of legs of said U-shaped spring member having an inturned portion, a longitudinal U-shaped spring member receiving groove in each said first and second jaw members, said longitudinal groove terminating rearwardly of said pivot pin and forming with the inturned ends of the U-shaped spring stop members for the U-shaped spring when the spring is in said first position, the bridge portion thereof in conjunction with said side flanges carried by said first jaw member providing a smoothly contoured hinge end thereby reducing to a minimum zones for the entrapment of tissue which might be the cause of adhesions.

2. A surgical clip as defined in claim 1 wherein the opposed surfaces of each jaw member are provided with a plurality of opposed meshing tube gripping elements.

3. The invention defined in claim 2 wherein said opposed alternate meshing elements comprises cooperating cones and conical bores.

4. The invention defined in claim 2 wherein said generally U-shaped spring member is of ribbon configuration and the remote faces of the jaw members are provided with elongated slots within which the ribbon-like U-shaped spring is adapted to slidably traverse.

5. The invention defined in claim 4 including turned in tip elements on said U-shaped spring and cooperating transverse slots in said grooves of each jaw member to secure the U-shaped spring when said spring is in the position to urge the jaw members into their closed position.

* * * * *